United States Patent
Yamato et al.

(10) Patent No.: US 11,152,578 B2
(45) Date of Patent: Oct. 19, 2021

(54) SULFONIUM SALTS OF DNTT AND RELATED COMPOUNDS AS SOLUBLE PHOTOCLEAVABLE PRECURSORS FOR ORGANIC SEMICONDUCTORS FOR USE IN ORGANIC FIELD-EFFECT TRANSISTORS

(71) Applicant: Clap Co., Ltd., Seoul (KR)

(72) Inventors: Hitoshi Yamato, Amagasaki (JP); Takuya Tsuda, Amagasaki X (JP); Iori Doi, Amagasaki (JP); Fabien Nekelson, Amagasaki (JP)

(73) Assignee: Clap Co., Ltd., Seoul (KR)

( * ) Notice: Subject to any disclaimer, the term of this patent is extended or adjusted under 35 U.S.C. 154(b) by 0 days.

(21) Appl. No.: 16/765,816

(22) PCT Filed: Nov. 13, 2018

(86) PCT No.: PCT/EP2018/081011
§ 371 (c)(1),
(2) Date: May 20, 2020

(87) PCT Pub. No.: WO2019/101569
PCT Pub. Date: May 31, 2019

(65) Prior Publication Data
US 2020/0388772 A1    Dec. 10, 2020

(30) Foreign Application Priority Data
Nov. 21, 2017 (EP) .................................... 17202733

(51) Int. Cl.
*H01L 51/00* (2006.01)
*C07D 495/04* (2006.01)
*H01L 51/05* (2006.01)

(52) U.S. Cl.
CPC ........ *H01L 51/0074* (2013.01); *C07D 495/04* (2013.01); *H01L 51/0003* (2013.01); *H01L 51/0026* (2013.01); *H01L 51/0545* (2013.01); *H01L 51/0566* (2013.01)

(58) Field of Classification Search
CPC ............ H01L 51/0074; H01L 51/0545; C07D 495/04
See application file for complete search history.

(56) References Cited

FOREIGN PATENT DOCUMENTS

| JP | 2008096680 A | 4/2008 |
|---|---|---|
| JP | 2009069381 A | 4/2009 |
| WO | WO2014115749 A1 | 7/2014 |

OTHER PUBLICATIONS

Kimura et al., "Soluble Organic Semiconductor Precursor With Specific Phase Separation for High-Performance Printed Organic Transistors," Adv Mater. (2015) 27(4): 727-732.

*Primary Examiner* — Anthony Ho
(74) *Attorney, Agent, or Firm* — Morrison & Foerster LLP

(57) ABSTRACT

The present invention provides a process for manufacturing an electronic device comprising a semiconducting layer, which process comprises i) a step of applying a composition comprising at least a compound of formulae (1A)-(1B)-(1C) on a precursor of the electronic device in order to form a layer, and ii) a step of treating the layer of step i) with light in order to form a semiconducting layer, we well as a compound of formula 1A, 1B or 1C, compositions comprising at least one compound of formula 1A, 1B or 1C, and the use of at least one compound of formula 1A, 1B or 1C as photocleavable precursor for organic semiconducting materials.

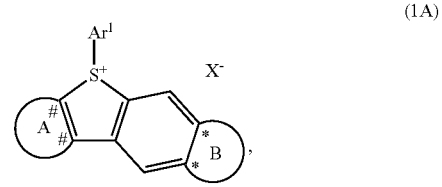

(1A)

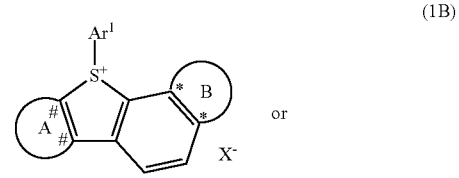

(1B)

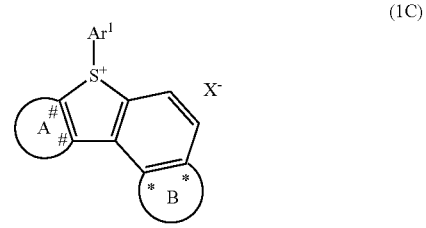

(1C)

15 Claims, No Drawings

SULFONIUM SALTS OF DNTT AND RELATED COMPOUNDS AS SOLUBLE PHOTOCLEAVABLE PRECURSORS FOR ORGANIC SEMICONDUCTORS FOR USE IN ORGANIC FIELD-EFFECT TRANSISTORS

CROSS REFERENCE TO RELATED APPLICATIONS

This application is a national stage application under 35 U.S.C. § 371 of International Application No. PCT/EP2018/081011, filed internationally on Nov. 13, 2018, which claims priority to European Patent Application No. 17202733.6, filed Nov. 21, 2017, the contents of which are incorporated herein by reference in their entirety.

The present invention relates to a process for preparing an electronic device, preferably an organic field effect transistor, to sulfonium compounds that are precursors of organic semiconducting materials and to compositions comprising these compounds.

Organic semiconducting materials can be used in electronic devices such as organic photovoltaic devices (OPVs), organic field-effect transistors (OFETs), organic light emitting diodes (OLEDs), and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

Furthermore, it is desirable that the semiconducting layer or a precursor layer to the semiconducting layer can be photopatterned, thus no additional step of applying another layer such as a photoresist layer for patterning the semiconducting layer is necessary.

Sulfonium compounds are known in the art.

JP2008-096680 describes compositions for manufacturing color filters containing at least one sulfonium salt of the following formulae

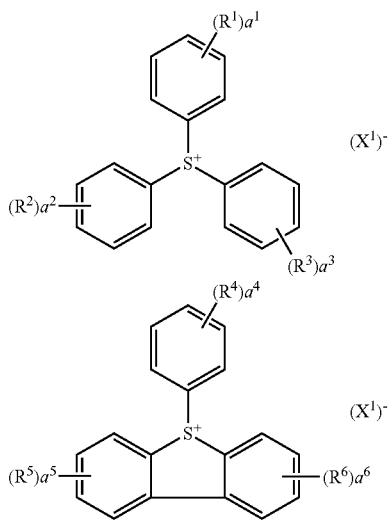

wherein $R^1$ to $R^3$ are substituents, $a^1$ is 0 to 5, $a^2$ and $a^3$ are 1 to 5, $R^4$ to $R^6$ are substituents, $a^4$ is 0 to 5, and $a^5$ and $a^6$ are 0 to 4 and $X^1$ is a negative anion, a photopolymerizable compound and a colorant. The sulfonium salt functions as photopolymerization initiator.

JP2009-069381 describes resist compositions comprising the following compound

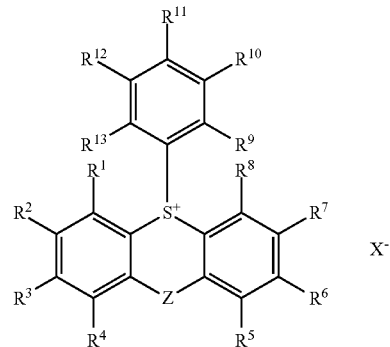

wherein Z is a single bond or a divalent group, and X is an anion, and a resin. The sulfonium salt functions as electron beam, x-ray or UV sensitive generator for generating an acid. The resin changes its solubility properties upon contact with the generated acid.

The use of soluble precursor compounds for forming the semiconducting material of an electronic device is known in the art.

Y. Kimura, T. Nagase, T. Kobayashi, A. Hamaguchi, Y. Ikeda, T. Shiro, K. Takimiya, H. Naito Adv. Mater. 2015, 27, 727 to 732 describes an organic thin film transistor OFET), wherein the semiconducting layer is formed by applying a solution of the NTT-precursor (5,14-N-phenylmaleimidedinaphtho[2,3-b:2',3'-f]-thieno[3,2-b] thiophene, followed by converting the DNTT-precursor to dinaphtho[2,3-b:2',3'-f]thieno[3,2-b]thiophene (DNTT) by annealing at temperatures of above 195° C.

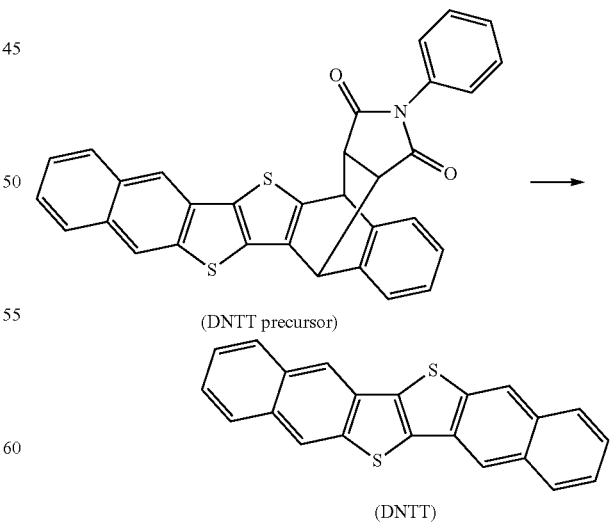

DNTT itself shows only a low solubility and cannot be applied by solution-processing techniques. The process of Y. Kimura is disadvantageous in that neither the semiconducting layer nor the precursor layer to the semiconducting layer can be photopatterned, thus an additional step of applying another layer such as a photoresist layer for patterning the semiconducting layer is necessary.

It was the object of the present invention to provide a process for the preparation of an electronic device comprising a semiconducting layer, which process is compatible with solution-processing techniques, and which process does not require an additional layer, such as a photoresist layer, in order to form a patterned semiconducting layer.

This object is solved by the process of claim 1, the compounds of claim 10 and the composition of claim 14.

The process of the present invention is a process for manufacturing an electronic device comprising a semiconducting layer, which process comprises
i) the step of applying a composition comprising at least a compound of formulae

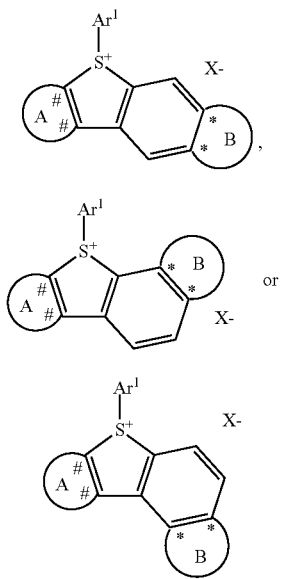

on a precursor of the electronic device in order to form a layer, and
ii) the step of treating the layer of step i) with light in order to form a semiconducting layer,
wherein
$Ar^1$ is $C_{6-14}$-aryl or 5 to 14-membered heteroaryl, which $C_{6-14}$-aryl and 5 to 14-membered heteroaryl can be substituted by one to three substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^1$ or CO, wherein $R^1$ is H or $C_{1-10}$-alkyl,
A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^a$ or CO, wherein $R^a$ is H or $C_{1-10}$-alkyl,
B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^b$ or CO, wherein $R^b$ is H or $C_{1-10}$-alkyl,
and
$X^-$ is an organic or inorganic anion.

Examples of $C_{6-14}$-aryl are phenyl, naphthyl, anthracenyl, phenantrenyl, tetracenyl and chrysenyl.

A 5 to 14 membered heteroaryl contains at least one heteroatom. Examples of 5 to 14-membered heteroaryl are

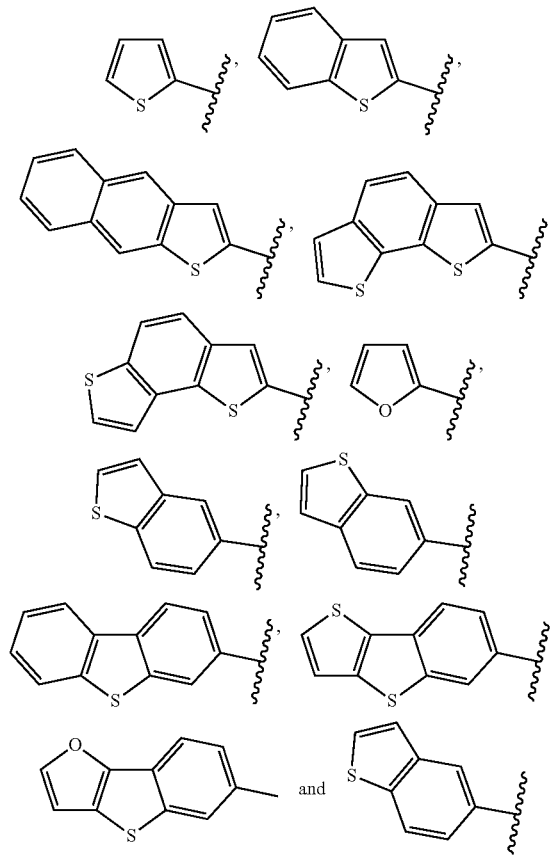

Examples of $C_{6-18}$ aromatic ring system, which includes the C-atoms marked with a #, are

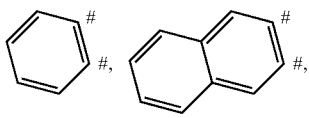

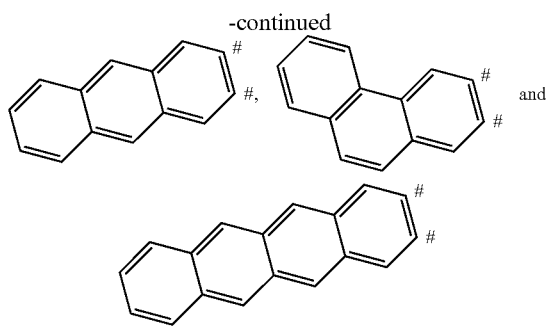

A 5 to 17-membered heteroaromatic ring system contains at least one heteroatom. Examples of 5 to 17-membered heteroaromatic ring system, which includes the C-atoms marked with a #, are

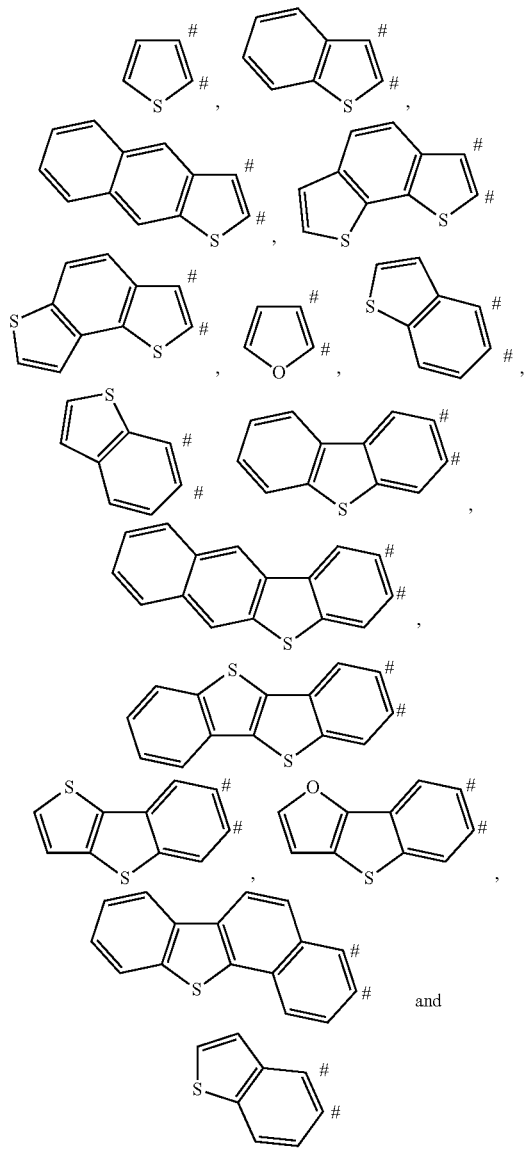

Examples of $C_{6-10}$ aromatic ring system, which includes the C-atoms marked with a @, are

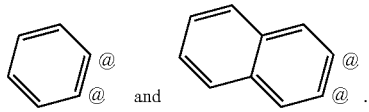 [SMILES: c1ccccc1 ; c1ccc2ccccc2c1]

Examples of $C_{6-14}$ aromatic ring system, which includes the C-atoms marked with a @, are $C_{6-10}$ aromatic ring system, which includes the C-atoms marked with a @, as outlined above and

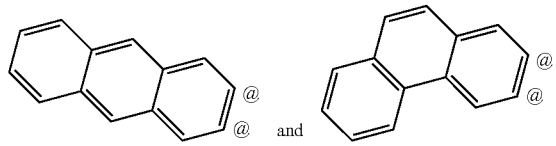

A 5 to 14-membered heteroaromatic ring system contains at least one heteroatom. Examples of 5 to 14-membered heteroaromatic ring system, which includes the C-atoms marked with a @, are

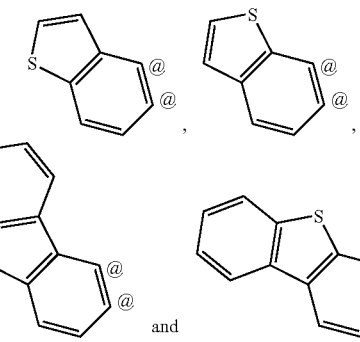

Examples of $C_{6-10}$ aromatic ring system, which includes C-atoms marked with a *, are

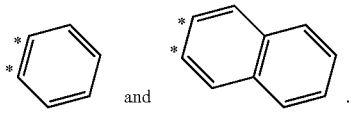 [SMILES: c1ccccc1 ; c1ccc2ccccc2c1]

Examples of $C_{6-14}$ aromatic ring system, which includes the C-atoms marked with a *, are $C_{6-10}$ aromatic ring system, which includes C-atoms marked with a *, as outlined above, and

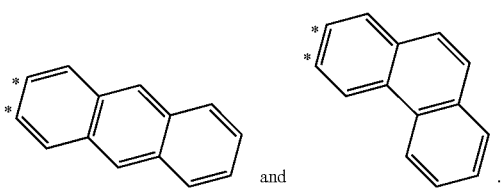

A 5 to 14-membered heteroaromatic ring system, which includes the C-atoms marked with a *, includes at least one heteroatom. Examples of 5 to 14-membered heteroaromatic ring system, which includes the C-atoms marked with a *, are

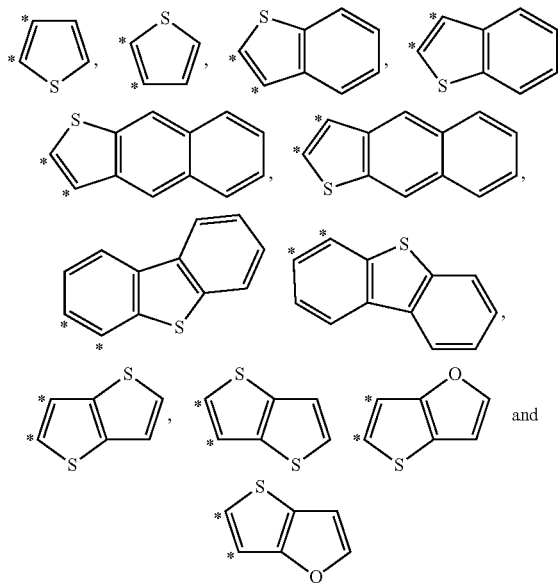

$C_{4-6}$-alkyl, $C_{1-10}$-alkyl, $C_{1-30}$-alkyl and $C_{3-20}$-alkyl can be branched or unbranched. Examples of $C_{4-6}$-alkyl are n-butyl, sec-butyl, isobutyl, tert-butyl, n-pentyl, neopentyl, isopentyl, n-(2,2-dimethyl)propyl, n-(1-ethyl)propyl and n-hexyl. Examples of $C_{1-10}$-alkyl are methyl, ethyl, n-propyl, isopropyl, n-butyl, sec-butyl, isobutyl, tert-butyl, n-pentyl, neopentyl, isopentyl, n-(2,2-dimethyl)propyl, n-(1-ethyl)propyl, n-hexyl, n-heptyl, 2-heptyl, n-octyl, 2-octyl, n-(3-methyl)heptyl, n-(1,1,3,3-tetramethyl)butyl, n-(2-ethyl)hexyl, n-nonyl, n-(1,1,3,3-tetramethyl)pentyl and n-decyl. Examples of $C_{1-30}$-alkyl are $C_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl, n-icosyl ($C_{20}$), n-docosyl ($C_{22}$), n-tetracosyl ($C_{24}$), n-hexacosyl ($C_{26}$), n-octacosyl ($C_{28}$) and n-triacontyl ($C_{30}$). Examples of $C_{3-20}$-alkyl are n-propyl, isopropyl, n-butyl, sec-butyl, isobutyl, tert-butyl, n-pentyl, neopentyl, isopentyl, n-(2,2-dimethyl)propyl, n-(1-ethyl)propyl, n-hexyl, n-heptyl, 2-heptyl, n-octyl, 2-octyl, n-(3-methyl)heptyl, n-(1,1,3,3-tetramethyl)butyl, n-(2-ethyl)hexyl, n-nonyl, n-(1,1,3,3-tetramethyl)pentyl and n-decyl n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$).

$C_{2-30}$-alkenyl can be branched or unbranched. Examples of $C_{2-30}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl, docenyl, linoleyl ($C_{18}$), linolenyl ($C_{18}$), oleyl ($C_{18}$), arachidonyl ($C_{20}$) and erucyl ($C_{22}$).

$C_{2-30}$-alkynyl can be branched or unbranched. Examples of $C_{2-30}$-alkynyl are ethynyl, 2-propynyl, 2-butynyl, 3-butynyl, pentynyl, hexynyl, heptynyl, octynyl, nonynyl, decynyl, undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of compounds of formula (1A) are

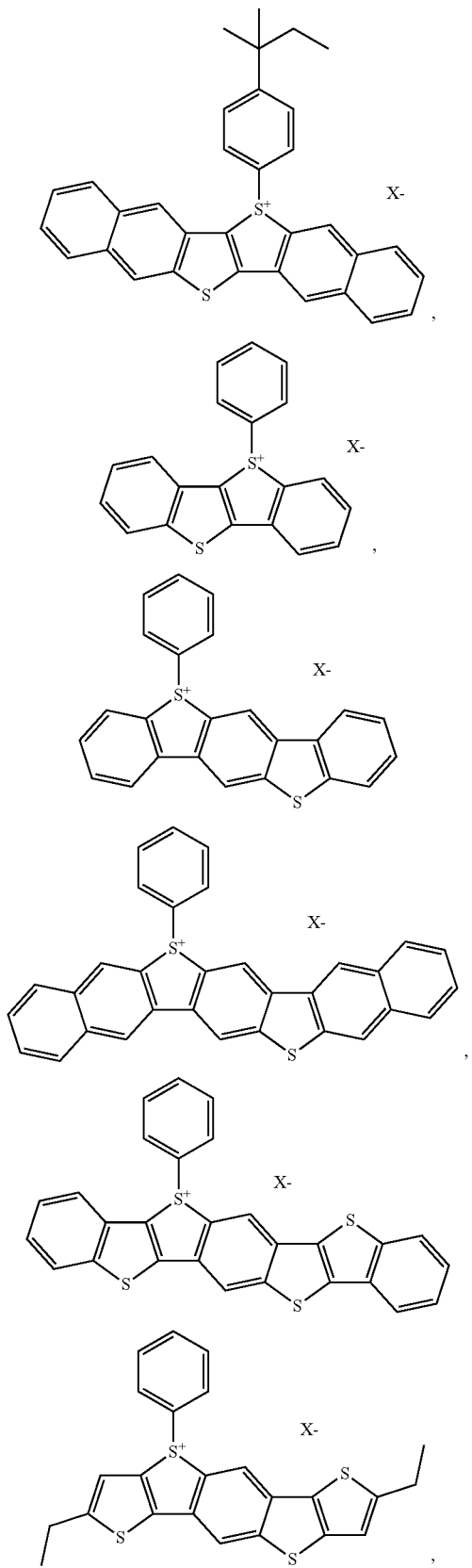

-continued

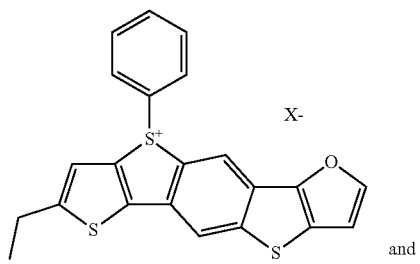

and

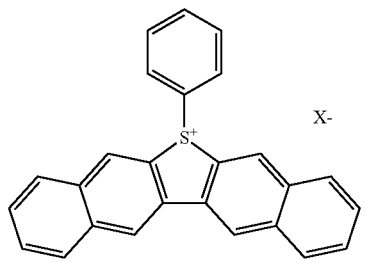

Examples of compounds of formula (1B) are

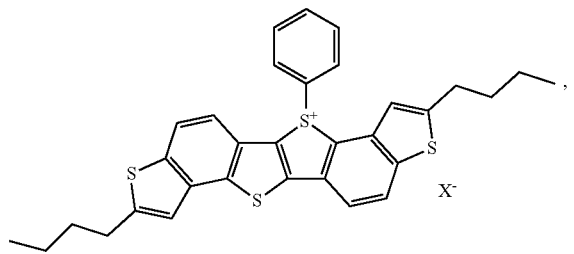

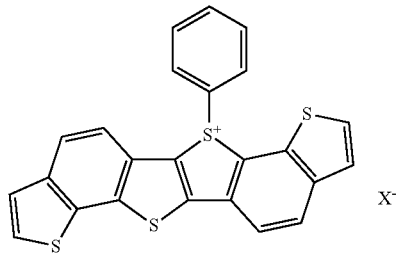

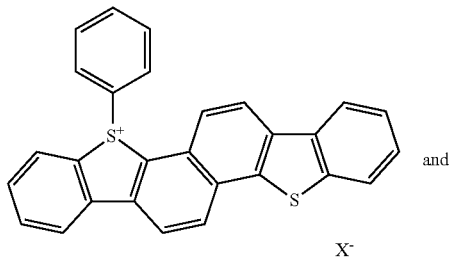

and

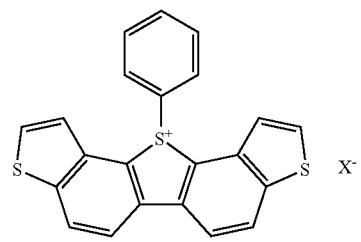

Examples of organic anions are

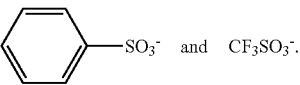 and $CF_3SO_3^-$.

Example of inorganic anions are $(F_4)^-$, $(PF_6)^-$, $(AsF_6)^-$ and $(SbF_6)^-$.

Preferably, $Ar^1$ is $C_{6-14}$-aryl or 5 to 14-membered heteroaryl, which $C_{6-14}$-aryl and 5 to 14-membered heteroaryl can be substituted by one to three substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl independently can be replaced by O, S, $NR^1$ or CO, wherein $R^1$ is H or $C_{1-10}$-alkyl, and wherein 5 to 14-membered heteroaryl contains one to four heteroatoms independently selected from the group consisting of S, O and $NR^2$, wherein $R^2$ is H or $C_{1-10}$-alkyl.

More preferably, $Ar^1$ is $C_{6-14}$-aryl or 5 to 14-membered heteroaryl, which $C_{6-14}$-aryl and 5 to 14-membered heteroaryl can be substituted by one to three substituents $C_{1-30}$-alkyl, and wherein 5 to 14-membered heteroaryl contains one to four heteroatoms independently selected from the group consisting of S and O.

Even more preferably, $Ar^1$ is phenyl, naphthyl or thiophenyl, which phenyl, naphthyl and thiophenyl can be substituted by one $C_{3-20}$-alkyl.

Most preferably, $Ar^1$ is phenyl, which can be substituted by one $C_{3-20}$-alkyl, for example $C_{4-6}$-alkyl such as n-(1,1-dimethyl)propyl.

Preferably, A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^a$ or CO, wherein $R^a$ is H or $C_{1-10}$-alkyl, and which 5 to 17-membered heteroaromatic ring system contains one to five heteroatoms independently selected from the group consisting of S, and $NR^3$, wherein $R^3$ is H or $C_{1-10}$-alkyl.

More preferably, A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to three substituents $C_{1-30}$-alkyl, and which 5 to 17-membered heteroaromatic ring system contains one to four heteroatoms independently selected from the group consisting of S and O.

Even more preferably, A is a 5 to 17-membered heteroaromatic ring system, which includes the C-atoms marked with a #, which 5 to 17-membered heteroaromatic ring system can be substituted by one to three substituents $C_{1-30}$-alkyl, and contains one to four heteroatoms independently selected from the group consisting of S and O.

Preferably, is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^b$ or CO, wherein $R^b$ is H or $C_{1-10}$-alkyl, and which 5 to 14-membered heteroaromatic ring system contains one to five heteroatoms independently selected from the group consisting of S, and $NR^4$, wherein $R^4$ is H or $C_{1-10}$-alkyl.

More preferably, B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O.

A preferred composition of the process of the present invention is a composition comprising at least a compound of formulae

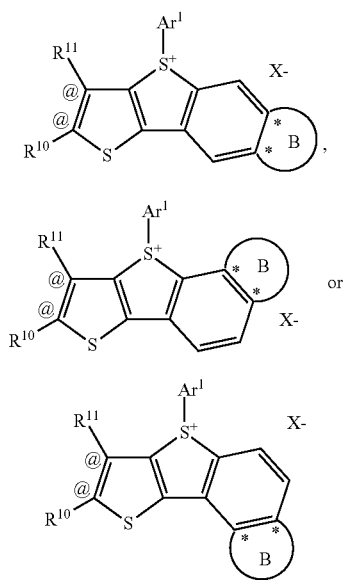

wherein
$Ar^1$, $X^-$ and B are as defined above, and
$R^{10}$ and $R^{11}$ are independently H or $C_{1-30}$-alkyl, or $R^{10}$ and R together with the C-atoms marked with a form a $C_{6-14}$-aromatic ring system, or $R^{10}$ and R together with C-atoms marked with a @ form a 5 to 14-membered heteroaromatic ring system, which $C_{6-14}$-aromatic ring system and 5 to 14-membered heteroaromatic ring system can be substituted with one to two substituent $C_{1-30}$-alkyl, and which 5 to 14-membered heteroaromatic ring system contains one to two heteroatoms S.

Preferably, $R^{10}$ and $R^{11}$ together with the C-atoms marked with a @ form a $C_{6-14}$-aromatic ring system, which $C_{6-14}$-aromatic ring system can be substituted with one to two substituent $C_{1-30}$-alkyl.

Preferably, $R^{10}$ and $R^{11}$ together with the C-atoms marked with a @ form a $C_{6-10}$-aromatic ring system, which $C_{6-10}$-aromatic ring system can be substituted with one to two substituent $C_{1-30}$-alkyl.

Preferably, B is $C_{6-14}$ aromatic ring system, which includes the C-atoms marked with a *, which $C_{6-14}$ aromatic ring system can be substituted by one to three substituents $C_{1-30}$-alkyl.

More preferably, B is $C_{6-10}$ aromatic ring system, which includes the C-atoms marked with a *, which $C_{6-10}$ aromatic ring system can be substituted by one or two substituents $C_{1-30}$-alkyl.

Most preferably, B is

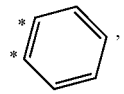

which can be substituted by one or two substituents $C_{1-30}$-alkyl.

A more preferred composition of the process of the present invention comprises at least a compound of formula

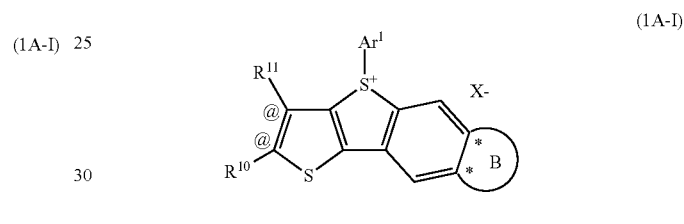

wherein $Ar^1$, B, $X^-$ and $R^{10}$ and $R^{11}$ are as defined above, and preferably $Ar^1$ is phenyl, naphthyl or thiophenyl, which phenyl, naphthyl and thiophenyl can be substituted by one $C_{3-20}$-alkyl, $R^{10}$ and $R^{11}$ together with the C-atoms marked with a @ form a $C_{6-10}$-aromatic ring system, which $C_{6-10}$-aromatic ring system can be substituted with one to two substituent $C_{1-30}$-alkyl, B is a $C_{6-10}$ aromatic ring system, which includes the C-atoms marked with a *, which $C_{6-10}$ aromatic ring system can be substituted by one or two substituents $C_{1-30}$-alkyl, and $X^-$ is an inorganic or organic anion.

The most preferred composition of the process of the present invention comprises at least a compound of formula

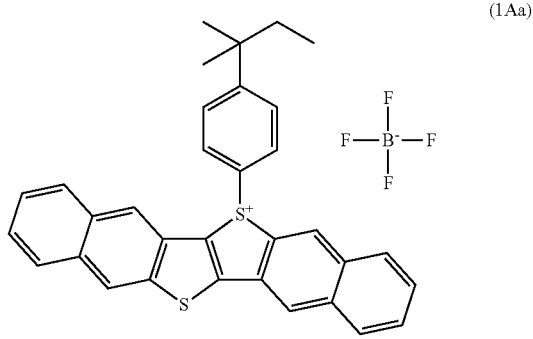 [SMILES: CCC(C)(C)c1ccc(-[s+]2c3cc4ccccc4cc3c3sc4cc5ccccc5cc4c32)cc1 ; F[B-](F)(F)F]

Compounds 1A, 1B and 1C can be prepared by methods known in the art.

For example, a compound of formula

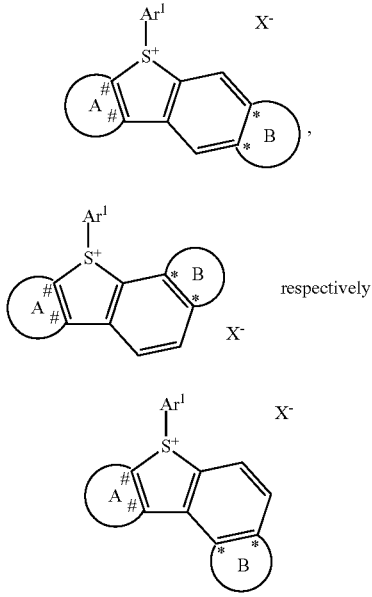

wherein Ar¹, A, B and X⁻ are as defined above,
can be prepared by treating a compound of formula

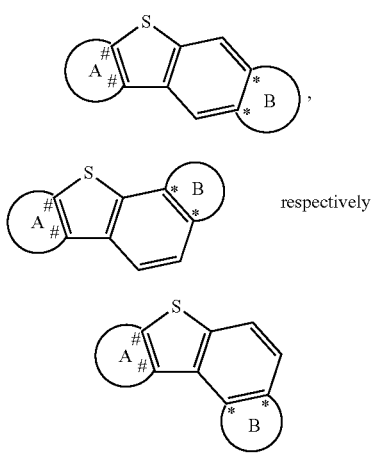

wherein A and B are as defined for the compounds of formula 1A, 1B, respectively 1C, with (Ar¹)₂I⁺X⁻, wherein Ar¹ and X⁻ are as defined for the compounds of formula 1A, 1B, respectively 1C, in the presence of CuSO₄.

Preferably, the reaction is performed at elevated temperatures such as at temperatures in the range of 160 to 20° C., and in the presence of a suitable solvent such as o-dichlorobenzene.

The compounds of formulae 2A, 2B and 2C can be prepared by methods known in the art. For example, the compound of formula

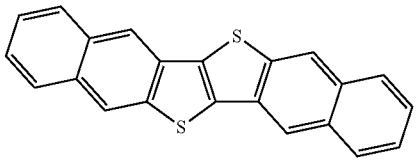

can be prepared as described by T. Yamamoto, K. Takimiya J. Am. Chem. Soc. 2007, 129, 2224 to 2225.

Preferably, X⁻ is an inorganic anion. More preferably, X⁻ is (BF₄)⁻.

The electronic device can be any electronic device. Preferably, the electronic device is an organic light emitting diode or an organic field effect transistor. More preferably, the electronic device is an organic field effect transistor.

Usually, an organic field effect transistor comprises a dielectric layer, a semiconducting layer and a substrate. In addition, an organic field effect transistor usually comprises a gate electrode and source/drain electrodes. The organic field effect transistor can be a top-gate or bottom-gate organic field effect transistor.

The dielectric layer comprises a dielectric material. The dielectric material can be inorganic such as silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BB), or polyimide (PI). The dielectric layer can have a thickness of 10 to 2000 nm, preferably of 50 to 1000 nm, more preferably of 100 to 800 nm. The inorganic dielectric materials are usually deposited by thermal evaporation. The dielectric materials that are organic polymers are usually applied as a composition comprising at least one solvent by solution-processing techniques such as spin-coating, ink-jet printing, gravure printing and roller-blade coating.

When the organic field effect transistor is a bottom-gate organic field effect transistor, the organic field effect transistor can also comprise a self-assembled monolayer of organic silane or organic phosphoric acid derivatives, which is usually between the dielectric layer and the semiconducting layer. An example of an organic silane derivative is octyl trichlorosilane or octadecyl trichlorosilane. An examples of an organic phosphoric acid derivative is octyldecylphosphoric acid. The organic silane or organic phosphoric acid derivatives are usually applied as compositions comprising at least one solvent such as toluene by solution-processing techniques such as spin-coating, ink-jet printing, gravure printing and roller-blade coating.

The composition comprising at least a compound of formulae 1A, 1B or 1C forms the semiconducting layer upon light treatment.

The composition comprising at least a compound of formulae 1A, 1B or 1C can be applied on the precursor of the organic field effect transistor by any known technique. Preferably, the composition comprising at least a compound of formulae 1A, 1B or 1C also comprises at least one solvent, such as chloroform, and is a solution. Preferably, the composition comprising at least a compound of formulae 1A, 1B or 1C and the at least one solvent, which composition is a solution, is applied by solution-processing techniques such as spin-coating, ink-jet printing, gravure printing and roller-blade coating.

The layer formed from the composition comprising at least a compound of formulae 1A, 1B or 1C is treated with light in order to form the semiconducting layer. Preferably, the light is ultraviolet light. Preferably, the light has a wavelength in the range of from 10 to 380 nm, more preferably in the range of from 280 to 380 nm.

The semiconducting layer can have a thickness of 5 to 500 nm, preferably of 10 to 100 nm, more preferably of 20 to 50 nm.

The precursor of the organic field effect transistor depends on the type of organic field effect transistor. If the organic field effect transistor is a bottom-gate organic field effect transistor, the precursor can comprise, in this order, a gate, a dielectric layer and a self-assembled monolayer.

The source/drain electrodes can be made from any suitable source/drain material, for example gold (Au) or tantalum (Ta). The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide, gold (Au) and/or tantalum (Ta). The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the type of the organic field effect transistor, the gate electrode, for example highly doped silicon can also function as substrate.

Preferably, all steps in the process of the present invention are performed at temperatures of below 150° C., more preferably of below 120° C., and most preferably, of below 100° C.

For example, a bottom-gate top-contact organic field effect transistor can be prepared as follows: The dielectric material, for example $Al_2O_3$ or silicon dioxide, can be applied as a layer on a gate electrode such as highly doped silicon wafer, which also functions as substrate, by a suitable deposition method such as atom layer deposition or thermal evaporation. A self-assembled monolayer of an organic phosphoric acid derivative or an organic silane derivative can be applied to the layer of the dielectric material. For example, a solution of the organic phosphoric acid derivative or the organic silane derivative in a suitable solvent such as toluene can be applied using solution-deposition techniques. The composition comprising at least a compound of formulae 1A, 1B or 1C and at least one solvent, for example, chloroform, can be applied by a solution-processing technique such as spin-coating. Source/drain electrodes can be formed by deposition of a suitable source/drain material, for example tantalum (Ta) and/or gold (Au), on the semiconducting layer through a shadow masks. The device can be treated with light, for example deep ultraviolet light. The device can be annealed at a temperature of 90° C. The channel width (W) is typically 500 to 1500 μm and the channel length (L) is typically 10 to 100 μm.

Also part of the resent invention is a compound of formulae

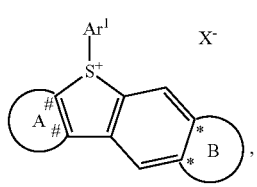

(1A)

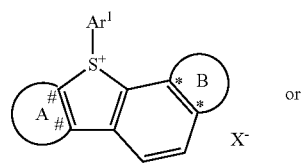

(1B)

or

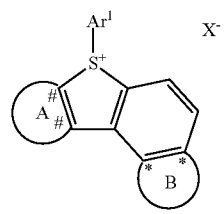

(1C)

wherein $Ar^1$ is $C_{6-14}$-aryl or 5 to 14-membered heteroaryl, which $C_{6-14}$-aryl and 5 to 14-membered heteroaryl can be substituted by one to three substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^1$ or CO, wherein $R^1$ is H or $C_{1-10}$-alkyl, A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^b$ or C, wherein $R^b$ is H or $C_{1-10}$-alkyl, B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by, S, $NR^5$ or CO, wherein $R^b$ is H or $C_{1-10}$-alkyl, and X— is an organic or inorganic anion, with the proviso that the compound of formula 1A, 1B or 1C is not

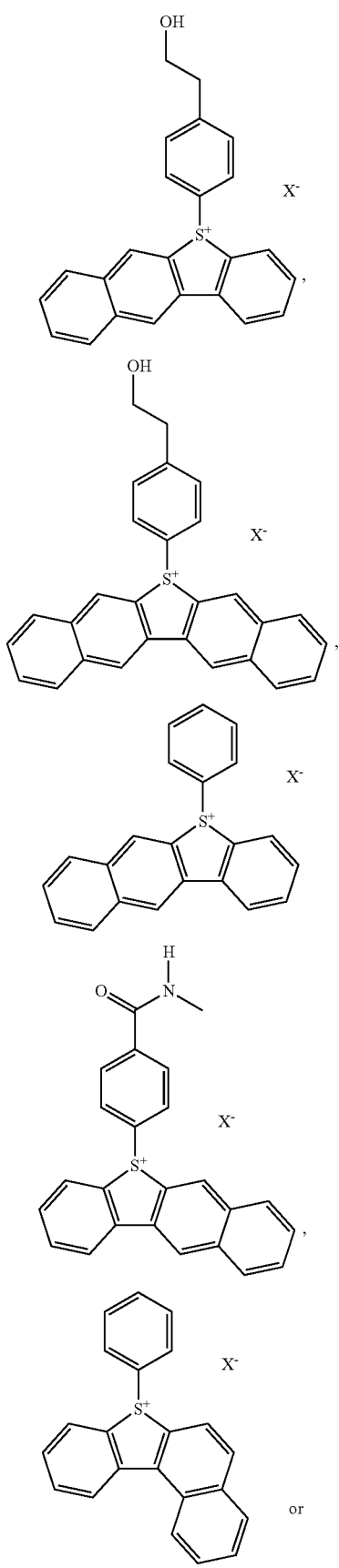

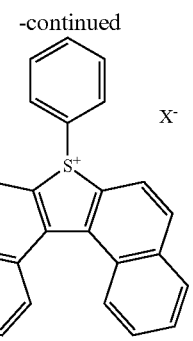

In referred compound of formula 1A, 1B or 1 of the present invention
$Ar^1$ is phenyl, naphthyl or thiophenyl, which phenyl, naphthyl and thiophenyl can be substituted by one $C_{3-20}$-alkyl,
A is a 5 to 17-membered heteroaromatic ring system, which includes the C-atoms marked with a #, which 5 to 17-membered heteroaromatic ring system can be substituted by one to three substituents $C_{1-30}$-alkyl, and contains one to four heteroatoms independently selected from the group consisting of S and O, and B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and $X^-$ is an organic or inorganic anion.

A preferred compound of formula 1A, 1B or 1C is a compound of formulae

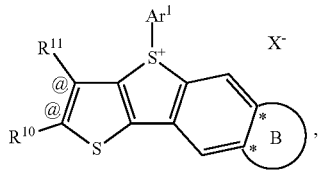
(1A-I)

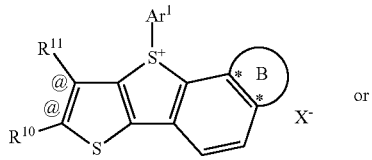
(1B-I) or

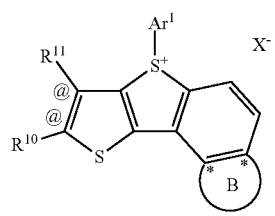
(1C-I)

wherein
$Ar^1$ is phenyl, naphthyl or thiophenyl, which phenyl, naphthyl and thiophenyl can be substituted by one $C_{3-20}$-alkyl,
B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and $R^{10}$ and $R^{11}$ are independently H or $C_{1-30}$-alkyl, or $R^{10}$ and $R^{11}$ together with the C-atoms marked with a @ form a $C_{6-14}$-aromatic ring system, or $R^{10}$ and $R^{11}$ together with C-atoms marked with a @ form a 5 to 14-membered heteroaromatic ring system, which $C_{6-14}$-aromatic ring system and 5 to 14-membered heteroaromatic ring system can be substituted with one to two substituent $C_{1-30}$-alkyl, and which 5 to 14-membered heteroaromatic ring system contains one to two heteroatoms S, and $X^-$ is an inorganic or organic anion.

In a preferred compound of formula 1A-I, 1B-I or 1C-I $Ar^1$ is phenyl, naphthyl or thiophenyl, which phenyl, naphthyl and thiophenyl can be substituted by one $C_{3-20}$-alkyl, B is $C_{6-10}$ aromatic ring system, which includes the C-atoms marked with a *, which $C_{6-10}$-aromatic ring system can be substituted by one to three substituents $C_{1-30}$-alkyl, and $R^{10}$ and $R^{11}$ together with the C-atoms marked with a @ form a $C_{6-14}$-aromatic ring system, which $C_{6-14}$-aromatic ring system can be substituted with one to two substituent $C_{1-30}$-alkyl, and $X^-$ is an inorganic or organic anion.

An even more preferred compound of the present invention is of formula

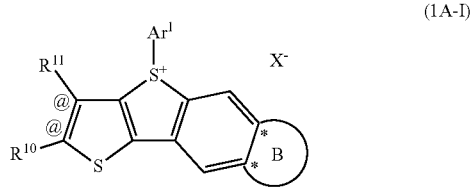

(1A-I)

wherein $Ar^1$ is phenyl, naphthyl or thiophenyl, which phenyl, naphthyl and thiophenyl can be substituted by one $C_{3-20}$-alkyl, B is $C_{6-10}$ aromatic ring system, which includes the C-atoms marked with a *, which $C_{6-10}$-aromatic ring system can be substituted by one to three substituents $C_{1-30}$-alkyl, and $R^{10}$ and $R^{11}$ together with the C-atoms marked with a @ form a $C_{6-14}$-aromatic ring system, which $C_{6-14}$-aromatic ring system can be substituted with one to two substituent $C_{1-30}$-alkyl, and $X^-$ is an inorganic or organic anion.

Preferably, B is

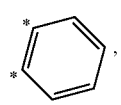

which can be substituted by one or two substituents $C_{1-30}$-alkyl.

The most preferred compound of the present invention is of formula

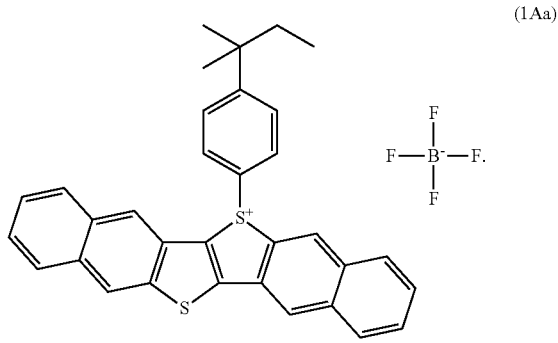 [SMILES: CCC(C)(C)c1ccc(-[s+]2c3cc4ccccc4cc3c3sc4cc5ccccc5cc4c32)cc1 ; F[B-](F)(F)F]

(1Aa)

Also part of the present invention are compositions comprising at least one compound of the present invention and at least one solvent. Preferably, the compositions of the present inventions are solutions.

Also part of the present invention is the use of at least one compound of the present invention as photocleavable precursor for organic semiconducting materials.

The process of the present invention for the preparation of an electronic device and the compounds of formulae 1A, 1B and 1C of the present invention, which are precursors of organic semiconducting materials, are advantageous in that the compounds of formulae 1A, 1B and 1C can be applied using solution processing techniques such as spin coating. Solution processing techniques are convenient from the point of processability, and allow the production of low cost organic semiconducting material-based electronic devices. In addition, the process of the present invention and the compounds of the present invention are advantageous in that the light treatment step that turns the compounds 1A, 1B and 1C into semiconducting material can be performed at temperatures of below 150° C., more preferably of below 120° C., and most preferably, of below 100° C., and thus allows the use of temperature sensitive plastic substrates, which are a pre-requisite for the production of light weight and mechanically flexible organic semiconducting material-based electronic devices. In addition, the process of the present invention and the compounds of the present invention are advantageous in that the soluble compounds 1A, 1B and 1C form an insoluble semiconducting layer upon light treatment and thus the light treatment step can be used for forming a patterned semiconducting layer. This renders an additional step of applying a photoresist laser in order to pattern the semiconducting layer obsolete. In addition, another layer can be applied on top of the insoluble semiconducting layer using solution-processing techniques without dissolving the semiconducting layer.

The compounds of formula 1A, 1B and 1C, and in particular those of 1A-I, 1B-I and 1C-I, are advantageous in that the compounds show high carrier mobilities.

FIG. 1 shows the drain-source current $I_{DS}$ in relation to the gate-source voltage $V_{GS}$ (transfer curve) for field effect transistor comprising a semiconducting material deriving from compound 1Aa at a drain-source voltage $V_{DS}$ of −80V is shown.

EXAMPLES

Example 1

Preparation Von Compound 1Aa

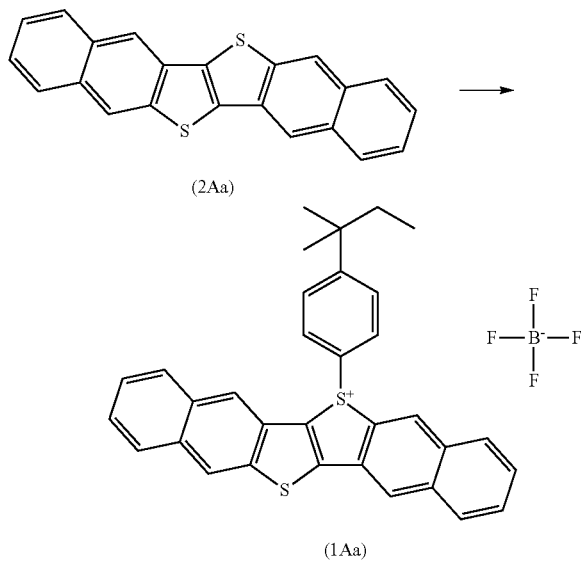

102 mg (0.3 mmol) of dinaphtho[2,3-b:2',3'-f]thieno[3,2-b]thiophene (2Aa or DNTT), 305 mg (0.6 mmol) of bis[4-(1,1-dimethylpropyl)phenyl]iodonium tetrafluoroborate, and 13 mg (0.06 mmol) of copper sulfate were added to 1 ml of o-dichlorobenzene, and stirred at 180° C. for 2.5 hours under $N_2$. After cooling to r.t., 30 ml of $CH_2Cl_2$ was added to solve the solid. Insoluble substance was removed by filtration, and 20 ml of tert-butylmethyl ether (t-BME) was added to the filtrate. The filtrate was concentrated by rotary evaporator to remove only $CH_2Cl_2$, resulting in crystallization of compound 1a The solid was isolated by filtration, washed with t-BME, yielding 146 mg (0.25 mmol; 85%) compound 1Aa as a greenish yellow solid. The structure was confirmed by the $^1$H-NMR and $^{19}$F-NMR spectrum ($CDCl_3$). δ [ppm]: 0.54 (t, 3H), 1.15 (s, 6H), 1.52 (q, 2H), 7.27-7.44 (m, 5H), 7.51 (t, 1H), 7.66-7.70 (m, 3H), 7.77-7.81 (m, 2H), 7.94-8.00 (m, 2H), 8.34 (d, 2H), 8.63 (s, 1H), and 149.1 (s, 4F).

Example 2

Comparing the Solubility of Compound 1Aa to Compound Compound 2Aa

The solubility of the compound 1Aa at 25° C. was compared to the solubility of compound 2Aa in various solvents. The results are outlined in the Table 1.

TABLE 1

| Compound | $CHCl_3$ | DMF | $CH_3CN$ |
|---|---|---|---|
| Compound 2Aa | <1 mg/ml | <1 mg/ml | <1 mg/ml |
| Compound 1Aa | 5 mg/ml | 8 mg/ml | 5 mg/ml |

Example 3

Preparation of an Organic Field-Effect Transistor Comprising a Semiconducting Material Deriving from Compound 1Aa as Precursor A heavily doped n-type silicon wafers with a thermally-grown silicon dioxide layer (200 nm) were cleaned with isopropanol and treated with a solution of octadecyl trichlorosilane in toluene. The solution of the compound 1Aa in chloroform was spin coated at 3000 rpm for 30 sec and annealed at 90° C. for 30 seconds. A 50 nm-thick of Au layer for source and drain electrodes was deposited through a shadow mask to give top contact OFET devices. The substrate was exposed to deep ultraviolet (UV) light (energy density of 2 $J/cm^2$) and annealed at 90° C. The channel width (W) was 1000 μm and channel length (L) was 62 μm. A sample without light exposure was also prepared and evaluated as a comparison.

All electrical measurements were performed in ambient air in the dark using a 4200-SCS Keithley parameter analyzer.

In FIG. 1 the drain-source current $I_{DS}$ in relation to the gate-source voltage $V_{GS}$ (transfer curve) for field effect transistor comprising a semiconducting material deriving from compound 1Aa at a drain-source voltage $V_{DS}$ of −80V is shown.

The field effect transistors comprising the semiconducting material deriving from compound 1Aa showed typical p-type characteristics.

The charge-carrier mobility (μ) was extracted in the saturation regime from the slope of $(I_{DS})^{1/2}$ versus $V_{GS}$ using the equation $μ=2 L/(W*Ci)*(dI_{DS}^{1/2}/dV_{GS})^2$, wherein L is the channel length, W is the channel width, Ci is the capacitance per unit area of the dielectric layer, $I_{DS}$ is the drain-source current, and $V_{GS}$ is the gate-source voltage.

The threshold voltage ($V_{th}$) was extracted from the intersection of the linear extrapolation of the $I_{DS}^{1/2}$ versus $V_{GS}$ plot with the $V_{GS}$ axis.

| | FIG. 1 | | | |
|---|---|---|---|---|
| Compound | UV exposure [mJ/cm$^2$] | Vth [V] | μ [cm$^2$/Vs] | I on/off |
| 1Aa | 0 | Not detected | Not detected | Not detected |
| 1Aa | 2000 | −38.2 | 0.003 | 1.0E+04 |

The invention claimed is:

1. A process for manufacturing an electronic device comprising a semiconducting layer, which process comprises
   i) a step of applying a composition comprising at least a compound of formulae

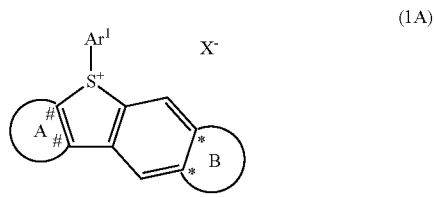

(1A)

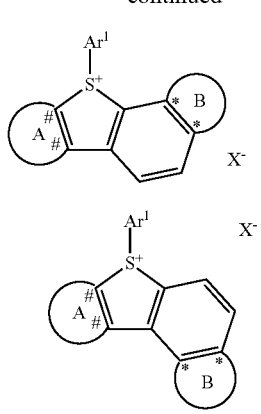

on a precursor of the electronic device in order to form a layer, and
  ii) a step of treating the layer of step i) with light in order to form a semiconducting layer,
  wherein
  $Ar^1$ is $C_{6-14}$-aryl or 5 to 14-membered heteroaryl, which $C_{6-14}$-aryl and 5 to 14-membered heteroaryl can be substituted by one to three substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^1$ or CO, wherein $R^1$ is H or $C_{1-10}$-alkyl,
  A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^a$ or CO, wherein $R^a$ is H or $C_{1-10}$-alkyl,
  B is a $C_{6-14}$ aromatic ring system, which includes the C-atoms marked with a *, or a 5 to 14 membered heteroaromatic ring system, which includes the C-atoms marked with a *, which $C_{6-14}$ aromatic ring system and 5 to 14-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^b$ or CO, wherein $R^b$ is H or $C_{1-10}$-alkyl,
  and
  $X^-$ is an organic or inorganic anion.

2. The process of claim 1, wherein
  $Ar^1$ is $C_{6-14}$-aryl or 5 to 14-membered heteroaryl, which $C_{6-14}$-aryl and 5 to 14-membered heteroaryl can be substituted by one to three substituents $C_{1-30}$-alkyl, and wherein 5 to 14-membered heteroaryl contains one to four heteroatoms independently selected from the group consisting of S and O,
  A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to three substituents $C_{1-30}$-alkyl, and which 5 to 17-membered heteroaromatic ring system contains one to four heteroatoms independently selected from the group consisting of S and O,
  B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and
  $X^-$ is an organic or inorganic anion.

3. The process of claim 2, wherein
  $Ar^1$ is phenyl, naphthyl or thiophenyl, which phenyl, naphthyl and thiophenyl can be substituted by one $C_{3-20}$-alkyl,
  A is a 5 to 17-membered heteroaromatic ring system, which includes the C-atoms marked with a #, which 5 to 17-membered heteroaromatic ring system can be substituted by one to three substituents $C_{1-30}$-alkyl, and contains one to four heteroatoms independently selected from the group consisting of S and O, and
  B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and
  $X^-$ is an organic or inorganic anion.

4. The process of claim 1, wherein the composition comprises at least a compound of formulae

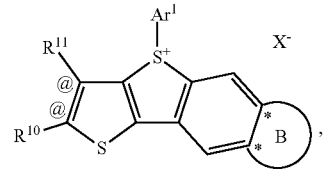

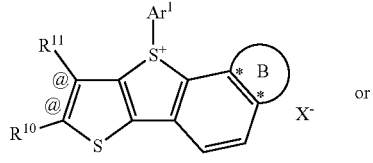

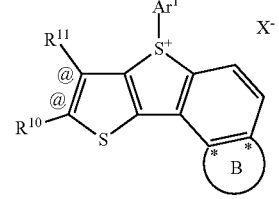

wherein
Ar¹ is phenyl, naphthyl or thiophenyl, which phenyl, naphthyl and thiophenyl can be substituted by one $C_{3-20}$-alkyl, B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and $R^{10}$ and $R^{11}$ are independently H or $C_{1-30}$-alkyl, or $R^{10}$ and $R^{11}$ together with the C-atoms marked with a @ form a $C_{6-14}$-aromatic ring system, or $R^{10}$ and $R^{11}$ together with C-atoms marked with a @ form a 5 to 14-membered heteroaromatic ring system, which $C_{6-14}$-aromatic ring system and 5 to 14-membered heteroaromatic ring system can be substituted with one to two substituent $C_{1-30}$-alkyl, and which 5 to 14-membered heteroaromatic ring system contains one to two heteroatoms S, and $X^-$ is an inorganic or organic anion.

5. The process of claim 4, wherein
Ar¹ is phenyl, naphthyl or thiophenyl, which phenyl, naphthyl and thiophenyl can be substituted by one $C_{3-20}$-alkyl, B is $C_{6-10}$ aromatic ring system, which includes the C-atoms marked with a *, which $C_{6-10}$-aromatic ring system can be substituted by one to three substituents $C_{1-30}$-alkyl, $R^{10}$ and $R^{11}$ together with the C-atoms marked with a @ form a $C_{6-14}$-aromatic ring system, which $C_{6-14}$-aromatic ring system can be substituted with one to two substituent $C_{1-30}$-alkyl, and $X^-$ is an inorganic or organic anion.

6. The process of claim 1, wherein the electronic device is an organic field effect transistor.

7. The process of claim 1, wherein the composition comprising at least a compound of formulae 1A, 1B or 1C also comprises at least one solvent.

8. The process of claim 1, wherein the light has a wavelength in the range of from 10 to 380 nm.

9. The process of claim 1, wherein all steps in the process for manufacturing the electronic device are performed at temperatures of below 150° C.

10. A compound of formulae

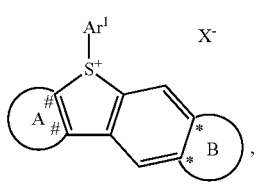
(1A)

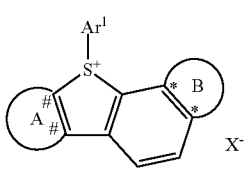
(1B)
or

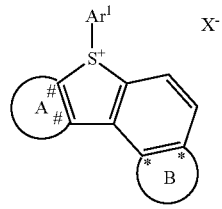
(1C)

wherein
Ar¹ is $C_{6-14}$-aryl or 5 to 14-membered heteroaryl, which $C_{6-14}$-aryl and 5 to 14-membered heteroaryl can be substituted by one to three substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^1$ or CO, wherein $R^1$ is H or $C_{1-10}$-alkyl, A is a $C_{6-18}$ aromatic ring system, which includes the C-atoms marked with a #, or a 5 to 17-membered heteroaromatic ring system, which includes the C-atoms marked with a #, which $C_{6-18}$ aromatic ring system and 5 to 17-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^a$ or CO, wherein $R^a$ is H or $C_{1-10}$-alkyl, B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to five substituents independently selected from the group consisting of $C_{1-30}$-alkyl, $C_{2-30}$-alkenyl, $C_{2-30}$-alkynyl, O—$C_{1-30}$-alkyl and S—$C_{1-30}$-alkyl, wherein one to four $CH_2$ groups of $C_{1-30}$-alkyl, $C_{2-30}$-alkenyl, $C_{2-30}$-alkynyl, O—$C_{1-30}$-alkyl, S—$C_{1-30}$-alkyl can independently be replaced by O, S, $NR^b$ or CO, wherein $R^b$ is H or $C_{1-10}$-alkyl, and $X^-$ is an organic or inorganic anion, with the proviso that the compound of formula 1A, 1B or 1C is not

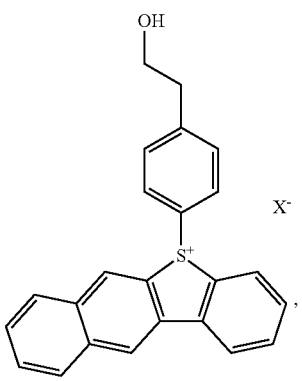

-continued

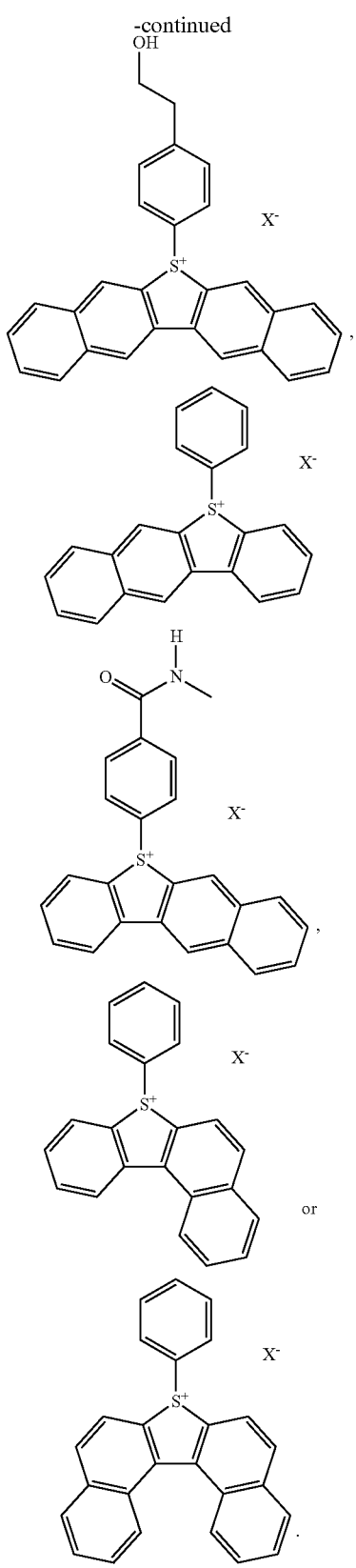

11. The compound of claim 10 wherein
Ar¹ is phenyl, naphthyl or thiophenyl, which phenyl, naphthyl and thiophenyl can be substituted by one $C_{3-20}$-alkyl, A is a 5 to 17-membered heteroaromatic ring system, which includes the C-atoms marked with a #, which 5 to 17-membered heteroaromatic ring system can be substituted by one to three substituents $C_{1-30}$-alkyl, and contains one to four heteroatoms independently selected from the group consisting of S and O, and B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and X⁻ is an organic or inorganic anion.

12. The compound of claim 11, wherein the compound of formula 1A, 1B or 1C is a compound of formulae

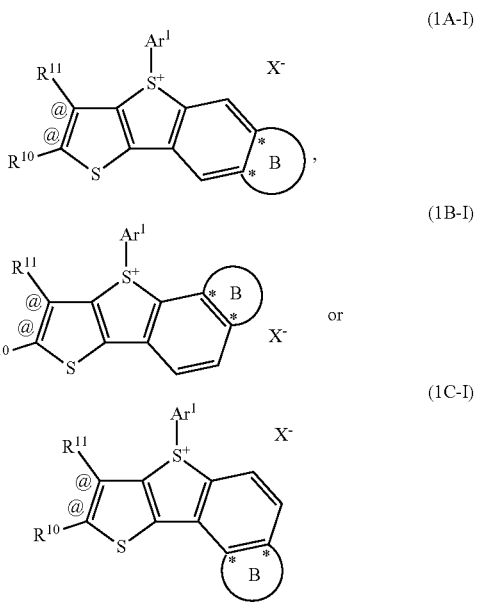

wherein
Ar¹ is phenyl, naphthyl or thiophenyl, which phenyl, naphthyl and thiophenyl can be substituted by one $C_{3-20}$-alkyl, B is a $C_{6-14}$ aromatic ring system, which includes the C-atoms marked with a *, or a 5 to 14-membered heteroaromatic ring system, which includes the C-atoms marked with a *, which $C_{6-14}$ aromatic ring system and 5 to 14-membered heteroaromatic ring system can be substituted by one to three substituents $C_{1-30}$-alkyl, and which 5 to 14-membered heteroaromatic ring system contains one to four heteroatoms independently selected from the group consisting of S and O, and $R^{10}$ and $R^{11}$ are independently H or $C_{1-30}$-alkyl, or $R^{10}$ and $R^{11}$ together with the C-atoms marked with a @ form a $C_{6-14}$-aromatic ring system, or $R^{10}$ and $R^{11}$ together with C-atoms marked with a @ form a 5 to 14-membered heteroaromatic ring system, which $C_{6-14}$-aromatic ring system and 5 to 14-membered heteroaromatic ring system can be substituted with one to two substituent $C_{1-30}$-alkyl, and which 5 to 14-membered heteroaromatic ring system contains one to two heteroatoms S, and X⁻ is an inorganic or organic anion.

13. The compound of claim 12, wherein $Ar^1$ is phenyl, naphthyl or thiophenyl, which phenyl, naphthyl and thiophenyl can be substituted by one $C_{3-20}$-alkyl, B is $C_{6-10}$ aromatic ring system, which includes the C-atoms marked with a *, which $C_{6-10}$-aromatic ring system can be substituted by one to three substituents $C_{1-30}$-alkyl, $R^{10}$ and $R^{11}$ together with the C-atoms marked with a @ form a $C_{6-14}$-aromatic ring system, which $C_{6-14}$-aromatic ring system can be substituted with one to two substituent $C_{1-30}$-alkyl, and $X^-$ is an inorganic or organic anion.

14. Compositions comprising at least a compound of claim 10 and at least one solvent.

15. Use of at least one compound of claim 10 as photocleavable precursor for organic semiconducting materials.

* * * * *